United States Patent [19]

Farrar et al.

[11] Patent Number: 4,556,728

[45] Date of Patent: Dec. 3, 1985

[54] SEPARATION OF METHANOL FROM MIXTURES CONTAINING IT

[75] Inventors: David Farrar; Gerald P. Benn, both of West Yorkshire, England

[73] Assignee: Allied Colloids Limited, England

[21] Appl. No.: 675,501

[22] Filed: Nov. 28, 1984

[30] Foreign Application Priority Data

Nov. 28, 1983 [GB] United Kingdom ............... 8331707

[51] Int. Cl.$^4$ ..................... C07C 67/03; C07C 29/92; C07C 31/04
[52] U.S. Cl. ..................................... 560/217; 568/923
[58] Field of Search ......................... 560/217; 568/923

[56] References Cited

U.S. PATENT DOCUMENTS

| | | | |
|---|---|---|---|
| 2,179,991 | 11/1939 | Bright et al. | 568/923 |
| 2,406,561 | 8/1946 | Rehberg | 560/217 |
| 3,574,712 | 4/1971 | Bloch et al. | 560/217 |
| 4,322,565 | 3/1982 | Dutson, Jr. et al. | 568/923 |
| 4,508,929 | 4/1985 | Sayles | 568/923 |

FOREIGN PATENT DOCUMENTS 206639 12/1982 Japan .................. 560/217

*Primary Examiner*—J. E. Evans
*Attorney, Agent, or Firm*—Lawrence Rosen

[57] ABSTRACT

A substantially anhydrous mixture of methanol with an organic compound with which it forms an azeotrope can be separated by dissolving into the mixture lithium chloride or other suitable salt that forms a complex with methanol so as to form a homogeneous mixture, adding an organic solvent that is miscible with the organic compound but immiscible with the complex and thereby forming a heterogeneous mixture, and separating the phases. The methanol can be recovered from one phase and the organic compound from the other. The organic compound may typically be methyl acrylate or methacrylate, the blend being, for instance, obtainable during the transesterification of methyl (meth)acrylate with an alcohol to form a higher boiling ester such as dimethylaminoethyl (meth)acrylate or 2-ethylhexyl acrylate.

11 Claims, No Drawings

SEPARATION OF METHANOL FROM MIXTURES CONTAINING IT

Methanol can usually be separated from a mixture containing it and another organic compound by simple distillation. However, methanol forms azeotropes with some organic compounds and so ordinary distillation cannot separate it from mixtures with such compounds. Examples of such compounds are methyl acrylate, or methacrylate and other low molecular weight esters, acetone, acrylonitrile and dichloroethane.

In British patent specification No. 980,053 an extractive distillation technique is described; in British patent specification No. 812,498 boric acid is reacted with the alcohol before distillation. Recently in British patent specification No. 1,422,694 a solvent extraction process has been described in which methanol is extracted into a methacrylic acid/acetic acid/water mixture while simultaneously methacrylic acid is separated.

It is well known that an azeotrope of an alcohol and an ester can be separated into two phases by addition of water, but both phases are then contaminated with water.

An important commercial process is the catalysed transesterification reaction of an alkanol with excess methyl (meth)acrylate to form a higher boiling ester. The product of this reaction is the higher boiling ester (e.g. dialkylamino alkyl ester of (meth)acrylic acid) together with methanol and unreacted methyl acrylate or methacrylate. The high boiling ester can be recovered by conventional techniques and this leaves a mixture of methanol and methyl (meth)acrylate. Burning this mixture is wasteful and it is desirable to reuse the ester in the reaction. If the separation is conducted in conventional manner by adding water it is necessary to dehydrate the resultant ester phase as otherwise the water that would be carried into the reaction with the ester will deactivate the catalyst.

It is known that azeotropes of water and organic solvents can be separated by salting out the organic compound by addition of an electrolyte. For instance in Industrial and Engineering Chemistry September 1944 pages 816 to 820 the effectiveness of various electrolytes, including lithium chloride and sodium chloride, is examined for separating water from methylethyl ketone. Upon addition of the salt to the aqueous-organic mixture the mixture separates into two phases, which may then be separated. Since salting out is a specific property of aqueous-organic systems, it is of no relevance to the problem of separating methanol from methyl acrylate or methacrylate or other azeotrope forming compound in the absence of water.

There is therefore a need for a method of separating methanol from a substantially anhydrous mixture with a low molecular weight ester or other organic compound with which it forms an azeotrope and that does not involve the compound becoming contaminated with water and that does not necessitate complicated distillation or dehydration steps.

A method according to the invention comprises dissolving into the mixture an inorganic salt that forms a complex with methanol and thereby forming a homogeneous mixture comprising the organic compound and the complex, adding an organic solvent that is miscible with the organic compound and immiscible with the complex and thereby forming a heterogeneous mixture, and separating the phases. The organic compound can be recovered from one phase and the methanol from the other phase.

Thus, in the invention a salt is added but instead of this causing a heterogeneous mixture, as in conventional salting out techniques, this forms a homogeneous mixture and the organic compound is then extracted from the homogeneous mixture by adding an organic solvent that converts the mixture into a heterogeneous mixture.

The inorganic salt must dissolve into the mixture of methanol and organic compound to form a homogeneous mixture containing sufficient of the salt to give useful separation during the extraction stage of the process. The salt must be one that is soluble in the mixture and forms a complex with methanol. It is generally a salt of a group I or group II metal, and is generally a halide. The preferred inorganic salt is lithium chloride but others that are useful include lithium bromide, lithium iodide, sodium iodide and calcium chloride. Other salts, such as sodium chloride, sodium bromide and magnesium sulphate, generally have rather poor solubility and so may give poor results.

The process is preferably conducted in the substantial absence of water. However, a very small amount may be tolerated and in some instances improves the extraction by the organic solvent. The amount of water is generally not more than 5%, and preferably below 1%, by weight of the mixture or not more than 6 mols, and usually not more than 1 mol, per mol inorganic salt. If the salt exists as a hydrate the amount of water is generally not more than the amount contained in such a hydrate, and the salt may be added in the form of this hydrate. Generally, however, the salt is added in anhydrous form.

The amount of salt will depend on the salt being used and on the components and proportions of the mixture being separated. Usually, the amount is from 1 to 100 grams, most preferably 5 to 40 grams, per 100 grams mixture. If the amount is too low, then it may not be possible to form a heterogeneous mixture upon addition of an appropriate organic solvent and so there will be no extraction. If the amount is too high, it may not dissolve into the mixture to form a homogeneous mixture.

The organic compound that is to be separated from methanol may be, for instance, acetone, acrylonitrile, dichlorethane but preferably it is a low molecular weight ester generally between a $C_{1-4}$ alkanol and a saturated or vinylic carboxylic acid, usually a $C_{1-5}$ acid. Often the ester is between a $C_{2-3}$ acid and a $C_{1-4}$ alkanol. Suitable compounds are methyl, ethyl and isopropyl acetates and methyl propionate but the preferred compounds are methyl acrylate and methyl methacrylate. The compound is generally a non-polar compound.

The organic solvent that is used as the extractant for the organic compound is usually non-polar and is preferably a hydrocarbon or chlorinated hydrocarbon. Suitable hydrocarbons are aromatic or aliphatic hydrocarbons containing 5 to 12, preferably 6 to 8, carbon atoms, most preferably hexane or xylene. Commercial blends of hydrocarbons are suitable, examples include white spirit, kerosene, the blend sold as Pale Oil 60 and the blend sold as SBP 11. Suitable chlorinated hydrocarbons are aliphatic materials such as perchloroethylene. Other suitable non-polar liquids include aliphatic esters such as methyl oleate and aromatic esters such as dibutylphthalate.

The process can be conducted simply by mixing the salt into the mixture of methanol and organic compound, generally at ambient temperature, either batch-wise or continuously, and then extracting this mixture with the organic solvent. This extraction can be conducted by means conventional for organic extraction processes, either batch-wise or continuously.

The organic compound can be recovered from the extract by, for instance, distillation and similarly methanol can be recovered from the raffinate by distillation, which will not only remove free methanol but will also release methanol from the complex. The distillation residue will consist mainly of a slurry or cake of the salt, and this can be reused.

Either or both of the distillates may be subjected again to the separation process of the invention. Generally, the organic compound obtained from the extract is sufficiently pure that it can be used without further purification, but the amount of organic compound with the methanol-containing distillate may be sufficiently high that further purification is desirable. Thus lithium chloride or other salt can be added to form a homogeneous mixture, and the mixture extracted with organic solvent as before.

The salt and extracting solvent are normally recycled with little or no loss of salt or solvent, and so the process can be operated substantially continuously as a substantially closed loop system.

The invention is of particular value in those processes where methyl (meth)acrylate is reacted with an alcohol in the presence of excess methyl (meth)acrylate and a transesterification catalyst (that is generally water sensitive) to form a mixture of a higher boiling ester, methyl (meth)acrylate and methanol. The higher boiling ester may be any ester that boils at a higher temperature than methyl methacrylate. Often the alcohol is a $C_{4-18}$ alkanol, thus forming a $C_{4-18}$ alkyl (meth)acrylate, such as 2-ethylhexyl acrylate. Alternatively the alcohol may be a dialkylamino alcohol such as dimethylamino ethanol, thereby forming a corresponding dialkylamino alkyl (meth)acrylate. In the invention this reaction is conducted in a first circuit and the resultant mixture of the higher boiling ester, methyl (meth)acrylate and methanol is separated by distillation into the higher boiling ester and a mixture of methyl (meth)acrylate and methanol and this mixture is separated in a second circuit by the process of the invention into methyl (meth)acrylate and methanol, the methanol is collected and the methyl (meth)acrylate is recycled to the first circuit. Within the second circuit, after adding the organic solvent and effecting phase separation, the phase containing organic solvent and ester is usually distilled to separate the ester and the organic solvent. The ester is recycled to the first circuit and the organic solvent is recycled within the second circuit. The phase containing the methanol complex is distilled to separate the methanol and the salt. The separated methanol may be recycled within the second circuit to effect further purification, before it is finally removed, and the salt is recycled in the second circuit.

In the following examples, the performance of the various salts and extractants was assessed by computing the Distribution Coefficient (D) and the Selectivity (S) where $$D = \frac{\text{conc. of ester in extract}}{\text{conc. of ester in raffinate}}$$

$$S = \frac{\text{Wt. of ester in extract}}{\text{Wt. of ester + methanol in extract}} \times 100$$

For maximum efficiency of extraction, both D and S should be as high as possible.

EXAMPLES 1-8

Various salts were added to the ester/alcohol mixture (13.5 kg MeOH, 31.5 kg methyl acrylate) and using xylene as extractant, values of D and S were obtained using GLC. The results are given in Table 1.

TABLE 1

| | Salt | Weight salt (g) per 100 g mixture | D | S |
|---|---|---|---|---|
| 1 | Anhydrous LiCl | 10 | 1.28 | 88.6 |
| 2 | Anhydrous LiCl | 20 | 1.33 | 89.2 |
| 3 | Anhydrous LiBr | 10 | 1.15 | 68.4 |
| 4 | Anhydrous LiBr | 20 | 1.08 | 83.2 |
| — | LiI.H$_2$O | 10 | miscible | |
| 5 | LiI.H$_2$O | 20 | 1.05 | 72.4 |
| 6 | CaCl$_2$ | 10 | 1.27 | 63.7 |
| 7 | CaCl$_2$ | 20 | 1.21 | 72.3 |
| — | NaI | 10 | miscible | |
| 8 | NaI | 20 | 0.97 | 66.7 |

Satisfactory values of D and S can be obtained when the methyl acrylate is replaced by methyl methacrylate.

EXAMPLE 9

When hexane was used as extractant and CaCl$_2$ as the salt at addition rates of 10 and 20 g/100 gm mixture of ester and alcohol, the values of D and S, were 1.03 and 73.6, and 0.85 and 81.7 respectively.

EXAMPLE 10

A large-scale multistage extraction was carried out using 20 g LiCl/100 gm methyl acrylate-methanol mixture used previously and 100 gm xylene as extractant. Further extraction of the raffinate produced the following results:

| No. of Extractions | D | S |
|---|---|---|
| 1 | 1.3 | 93.0 |
| 2 | 1.5 | 95.5 |
| 3 | 1.4 | 93.7 |

Following the three extractions the combined extract contained 96.5% of the total methyl acrylate and 12.1% methanol. The raffinate contained 87.9% of the methanol and only 3.5% of the original methyl acrylate.

In a typical commercial process incorporating this example, excess methyl acrylate is reacted with dimethylamino ethanol in the presence of a transesterification catalyst to form a reaction mixture containing dimethylaminoethyl acrylate, methyl acrylate and methanol. A blend of methyl acrylate and methanol is separated from this mixture by distillation and is then separated, in accordance with the detailed process described above, in a second circuit. The methyl acrylate separated in this second circuit is recycled to the reaction in the first circuit, the methanol is removed, and the lithium chloride and xylene are both recycled within the second circuit for reuse.

EXAMPLE 11

To 100 g of the azeotrope of methanol and acrylonitrile, whose composition was 61.3% and 38.7% respectively, was added 12.3 g of anhydrous lithium chloride. A homogeneous mixture was obtained which was then extracted with 100 g of xylene. The two layers were separated, weighed and analysed for methanol and acrylonitrile. D=0.833 and S=74.2%.

EXAMPLE 12

To 100 g of the azeotrope of methanol and acetone, whose composition was 12% and 88%, was added 2.1 g of anhydrous lithium chloride. A homogeneous mixture was obtained which was then extracted with 100 g of xylene. The two layers were separated, weighed and analysed for methanol and acetone. D=0.992 and S=94.7%.

We claim:

1. A method of separating methanol from a substantially anhydrous mixture with an organic compound with which it forms an azeotrope, characterised in that the method comprises dissolving into the mixture an inorganic salt that forms a complex with methanol thereby forming a homogeneous mixture comprising the organic compound and the complex, adding an organic solvent that is miscible with the organic compound and immiscible with the complex and thereby forming a heterogeneous mixture, and separating the phases.

2. A method according to claim 1 in which the salt is soluble in the mixture and forms a complex with methanol and is a salt of a group I or group II metal.

3. A method according to claim 1 in which the salt is selected from lithium chloride, lithium bromide, lithium iodide, sodium iodide and calcium chloride.

4. A method according to claim 1 in which the homogeneous mixture is free of water or in which the salt may exist as a hydrate and the mixture contains water in an amount not more than the amount contained in such a hydrate.

5. A method according to claim 1 in which the amount of salt is from 5 to 40 grams per 100 grams of the mixture of methanol and organic compound and is sufficient for the formation of a heterogeneous mixture upon addition of the organic solvent.

6. A method according to claim 1 in which the organic compound is selected from acetone, acrylonitrile, dichloroethane and low molecular weight esters formed between $C_{1-4}$ alkanols and $C_{1-5}$ carboxylic acids.

7. A method according to claim 1 in which the organic compound is methyl acrylate or methyl methacrylate.

8. A method according to claim 1 in which the organic solvent is a non-polar solvent selected from aliphatic esters, aromatic esters, aliphatic chlorinated hydrocarbons and aliphatic or aromatic hydrocarbons containing up to 12 carbon atoms.

9. A method according to claim 1 in which the organic compound is recovered from one phase by distillation and the raffinate containing methanol is distilled to release methanol from the complex and to remove freed methanol.

10. A method according to claim 1 in which the salt is recovered from one phase, the organic solvent is recovered from the other phase and the salt and organic solvent are recycled.

11. A method according to claim 1 in which, in a first circuit, methyl (meth)acrylate is reacted with an alcohol in the presence of excess methyl (meth)acrylate and a transesterification catalyst to form a mixture of a higher boiling ester, methyl (meth)acrylate and methanol, a mixture of methyl (meth)acrylate and methanol is separated from this mixture, in a second circuit the inorganic salt is added to this mixture to form the homogeneous mixture, the organic solvent is added to form the heterogeneous mixture and the phases are separated, methyl (meth)acrylate is recovered from one phase and is recycled to the first circuit and, within the second circuit, the organic solvent and the salt are recovered and recycled.

* * * * *